United States Patent
Dixon et al.

(10) Patent No.: US 7,610,130 B1
(45) Date of Patent: Oct. 27, 2009

(54) PHYSICAL CONTEXT MANAGEMENT FOR A MOTOR VEHICLE

(75) Inventors: Kevin R. Dixon, Albuquerque, NM (US); James C. Forsythe, Sandia Park, NM (US); Carl E. Lippitt, Albuquerque, NM (US); Lois Diane Lippitt, legal representative, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 615 days.

(21) Appl. No.: 11/489,833

(22) Filed: Jul. 20, 2006

Related U.S. Application Data (60) Provisional application No. 60/700,862, filed on Jul. 20, 2005.

(51) Int. Cl.
*G06F 19/00* (2006.01)
*A61B 5/00* (2006.01)

(52) U.S. Cl. .......................................... 701/36; 701/45

(58) Field of Classification Search ........................ None
See application file for complete search history.

(56) References Cited

U.S. PATENT DOCUMENTS

| | | | |
|---|---|---|---|
| 5,978,737 A * | 11/1999 | Pawlowski et al. .......... 701/301 |
| 6,266,589 B1 * | 7/2001 | Boies et al. ..................... 701/36 |
| 6,599,243 B2 * | 7/2003 | Woltermann et al. ......... 600/300 |
| 6,731,925 B2 * | 5/2004 | Naboulsi ...................... 455/345 |
| 7,039,551 B2 * | 5/2006 | Shu et al. ...................... 702/182 |
| 7,064,656 B2 * | 6/2006 | Belcher et al. ........... 340/425.5 |
| 7,477,135 B2 * | 1/2009 | Belcher et al. ........... 340/425.5 |
| 2004/0088095 A1 * | 5/2004 | Eberle et al. ................... 701/45 |
| 2005/0234617 A1 * | 10/2005 | Kynast et al. .................. 701/36 |

FOREIGN PATENT DOCUMENTS

JP    11-55417    *   2/1999

OTHER PUBLICATIONS

Schroedl, S.; Towards learning adaptive workload maps; Proc. of Intelligent Vehicles Symposium, 2002; IEEE; Jun. 9-11, 2003; pp. 627-632.*
McCall et al.; Visual context capture and analysis for driver attention monitoring; 2004 IEEE Intelligent Transportation Systems Conf; Washington, DC; Oct. 3-6, 2004; pp. 332-337.*

(Continued)

*Primary Examiner*—Michael J. Zanelli
(74) *Attorney, Agent, or Firm*—Madelynne J. Farber (57) ABSTRACT

Computer software for and a method of enhancing safety for an operator of a motor vehicle comprising employing a plurality of sensors of vehicle and operator conditions, matching collective output from the sensors against a plurality of known dangerous conditions, and preventing certain activity of the operator if a known dangerous condition is detected.

26 Claims, 4 Drawing Sheets

OTHER PUBLICATIONS

Bruns, A., et al., "EEG- and Context-Based Cognitive-State Classifications Lead to Improved Cognitive Performance While Driving", *Proceedings of the 1st International Conference on Augmented Cognition*, 2005, (Jul. 2005).

Forsythe, Chris, et al., "Toward a Human Emulator: A Framework for the Comprehensive Computational Representation of Human Cognition", *Proceedings of the 11th Conference on Computer-Generated Forces and Behavior Representation*, 2002.

Pomerleau, D., "Efficient Training of Artificial Neural Networks for Autonomous Navigation", *Neural Computation*, vol. 3, No. 1, (1991), pp. 88-97.

Stengel, R. F., "Stochastic Optimal Control: Theory and Applications", *Wiley-Interscience* (publisher) New York, Textbook,(1986).

Thorpe, C., et al., "Vision and Navigation for the Carnegie-Mellon Navlab", *IEEE Transactions and Pattern Analysis and Machine Intelligence* vol. 10, No. 3, (1988), pp. 362-373.

* cited by examiner

PHYSICAL CONTEXT MANAGEMENT FOR A MOTOR VEHICLE

CROSS-REFERENCE TO RELATED APPLICATIONS

This application claims priority to and the benefit of the filing of U.S. Provisional Patent Application Ser. No. 60/700,862, entitled "Physical Context Management for an Automobile", filed on Jul. 20, 2005, and the specification thereof is incorporated herein by reference.

STATEMENT REGARDING FEDERALLY SPONSORED RESEARCH OR DEVELOPMENT

The Government has rights to this invention pursuant to Contract No. DE-AC04-94AL85000 awarded by the U.S. Department of Energy.

INCORPORATION BY REFERENCE OF MATERIAL SUBMITTED ON A COMPACT DISC

Not Applicable.

COPYRIGHTED MATERIAL

© 2005-2006 Sandia Corporation. A portion of the disclosure of this patent document and of the related application listed above contains material that is subject to copyright protection. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention (Technical Field)

The present invention relates to methods, computer software, and apparatuses for determining conditions affecting operation of a motor vehicle.

2. Description of Related Art

During driving, as in many real-world tasks, humans engage in multitasking such as talking on the telephone, following instructions, and responding to requests. The present invention provides a system that minimizes the impact of untimely interruptions by providing a physical context to the driving conditions. By mitigating unnecessary tasks during periods of high difficulty, one can improve both driving, by minimizing hazards to safety, and the ability to successfully complete extraneous tasks. For example, talking on a mobile phone increases the likelihood of a traffic accident about 400%, depending on driving difficulty, which is a similar rate to intoxicated driving. A system that, for instance, delayed mobile phone calls during potentially difficult driving situations, such as merging onto a high-speed roadway, could drastically reduce the accident rate, while delaying those important conversations by a short time. The first step toward realizing such a system is the ability to correctly identify potentially difficult driving conditions.

BRIEF SUMMARY OF THE INVENTION

The present invention is of computer software for and a method of enhancing safety for an operator of a motor vehicle comprising: employing a plurality of sensors of vehicle and operator conditions; matching collective output from the sensors against a plurality of known dangerous conditions; and preventing certain activity of the operator if a known dangerous condition is detected. In the preferred embodiment, matching employs a nonlinear dynamical system. One embodiment matches against a plurality of conditions known a priori but as determined from a plurality of test subjects experiencing simulations of those conditions and from the sensor data received during recording of those simulations. Preferably an optimal solution of a learning algorithm of the nonlinear dynamical system has been calculated and in the matching step false negatives are substantially reduced in the calculation of an optimal solution via a method such as gradient-descent or genetic algorithm. The known conditions can alternatively be determined automatically from collected sensor data of those conditions and from concomitant human-scored difficulty estimates. In this case, unsupervised learning is preferably employed from collected sensor data of those conditions and from concomitant human-scored difficulty estimates. This preferably involves matching against a plurality of known conditions as determined via unsupervised learning employing linear regression of a 2*N dimensional vector of sensor input from N sensors. The operator can then make difficulty estimates concerning current conditions, which estimates are then incorporated into the matching step. Prevented activities can include employing a telephone, listening to audio programs, listening to high-volume audio programs, and employing vehicle interior lighting.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of classification systems, methods, and computer software to identify driving situations from labeled examples of previous occurrences. The purpose of the classifier is to provide physical context to a separate system that mitigates unnecessary distractions, allowing the driver to maintain focus during periods of high difficulty.

In one embodiment, while watching videos of driving, different users were asked to indicate their perceptions of the current situation. A classifier was trained to emulate the human recognition of driving situations. In unstructured conditions, such as driving in urban areas and the German autobahn, the classifier was able to correctly predict human perceptions of driving situations over 95% of the time.

The second embodiment advances the first in the following ways: It eliminates the need to determine a priori the useful contexts. The second embodiment automatically identifies the salient patterns, or "contexts" in the data. Since the contexts are automatically identified from the data itself, the system can be redeployed quickly to new operating environments (e.g., transitioning from on-road to off-road conditions). As a corollary, the second embodiment eliminates the concern about which contexts to identify. For example, are developers not identifying a context that could be potentially useful? This question is eliminated as the second embodiment automatically finds the statistical regularities in the data.

Using the first embodiment, difficulty estimates were conducted in an ad hoc manner. The new system allows one to construct optimal difficulty estimates using the contexts as inputs and human-generated estimates of perceived difficulty as the ground truth. The difficulty estimator then minimizes the error between its predictions and those of the human.

The first embodiment also did not allow adaptation to new users. The classifier was created from a set of training data, and is thereafter a static system. The second embodiment allows automatic adaptation to new users.

The first embodiment of the invention is next described in detail.

The test vehicle for experiments employed with the first embodiment of the invention was a Mercedes-Benz S-Class sedan, equipped with specialized sensors for the present research. The vehicle supplies a wide range of physical data such as speed, turn signals, etc. The posture of the driver is measured by a pressure-sensitive chair and ultrasonic six-degree-of-freedom head-tracking system, both developed by the University of Pittsburgh. Several hours of data were collected in unstructured driving conditions in both urban areas and on the German autobahn. Humans were also asked humans to label videos of these driving runs according to a list of potential situations. Consequently, the high-level goal of the work was to predict the time-series of human-recognized situations using the various sensors as input. To this end, the Sandia Cognitive Framework (SCF) as described in C. Forsythe and P. G. Xavier, "Human emulation: Progress toward realistic synthetic human agents," in *Proceedings of the 11th Conference on Computer-Generated Forces and Behavior Representation*, 2002, was employed to integrate the information of the driver posture and vehicle state to estimate the current driving situations. The pattern-recognition component of SCF is a type of Nonlinear Dynamical System (NDS). The present invention comprises the learning algorithms used to tune the parameters of the NDS to recognize driving situations.

A series of experiments was conducted to ascertain the most useful situations to provide the mitigation strategy with the appropriate driving context. As the goals of the mitigation strategy evolved, its information requirements changed accordingly. For example, during what driving situations would a driver least desire to receive a mobile phone call? Conversely, during what driving situations does a mobile phone call least impact safety? The questions were repeated for each extraneous task that the driver may encounter. In this manner, a list of potentially useful situations were identified and, in later stages, superfluous situations were removed from the list. After several iterations, the remaining situations are assumed to be the minimum set needed to perform the desired classifications and demonstrate an operational performance gain by mitigating extraneous tasks during difficult driving conditions. When the classifier of the invention indicates that the driving context is no longer difficult, mitigation ends and the vehicle operates normally. Typically, the driver is unaware that the system proactively intervened on her behalf.

Five human subjects were instructed to drive on a predefined circuit of German roads measuring about 200 km, ranging from urban streets to the autobahn, and each subject made three runs of the circuit. No modifications were made to the roadways or the ambient driving conditions, such as traffic or road construction. Data from the vehicle and driver posture were sampled at a rate of four Hertz. From these data-collection experiments, a total of almost 24 hours of data (343,946 samples) was obtained. In addition to the sensor streams, a wide-angle video camera was also used to capture a driver-like perspective out the front of the vehicle.

In order to use supervised learning to classify the data according to driving situations, it is first necessary to obtain ground-truth labels. As mentioned earlier, candidate situations were vetted by the information required by the mitigation strategy. After several iterations, the following situations were decided to be the most useful: (1) Approaching or Waiting at Intersection; (2) Leaving Intersection; (3) Entering On-ramp or High-Speed Roadway; (4) Being Overtaken; (5) High Acceleration or Dynamic State of Vehicle; (6) Approaching Slow-Moving Vehicle; (7) Preparing to Change Lanes; and (8) Changing Lanes.

To generate the labels, a tool was created that displayed to the human labeler the frontal video as well as a set of checkboxes, one for each of the eight candidate driving situations. The human labeler indicated their perception of the current driving situation by checking and unchecking the appropriate boxes. The tool also allowed the user to rewind, pause, save, load, and correct previously labeled time periods. After the user completed the labeling of a video segment, a zero-order hold was performed to associate a label with each input sample. This resulted in a sequence of binary vectors, $\{x^*_0, \ldots, x^*_N\}$ where $\lfloor x^*_n \rfloor_i = 1$ if the ith situation was active at time n, and $\lfloor x^*_n \rfloor_i = 0$ otherwise. Two users generated labels for each of the five driver subjects for each of their three circuits, for a total of 15 labeled data sets.

Formulated as a supervised-learning problem, a goal of the first embodiment of the present invention was to find an "optimal" mapping from a time-series of sensory inputs to a time-series of driving-situation labels. Since a goal of the invention is human centric, deriving a classifier that emulates the human recognition of driving situations, the Sandia Cognitive Framework (SCF) was employed. From an engineering perspective, the situation-recognition component of SCF is a type of Nonlinear Dynamical System (NDS). The inputs to the NDS are the processed sensory inputs, described above. The outputs of the NDS are estimated activation levels of the various situations as a function of time. The estimated situation activations can be considered a trajectory through the state space of the NDS. It is preferred to use the ordered sequence of labels, described above, as the groundtruth targets for a learning algorithm. From this formulation, the goal of a supervised-learning algorithm is to tune the parameters of the NDS to minimize the error between the estimated situations and the ground-truth situations generated by the human labelers.

To derive the preferred learning algorithm, one needs a few elementary functions and notation. One writes the (i,j)th entry of a matrix as $[A]_{i,j}$ and the ith entry of a vector as $[x]_i$.

Figure 1A:
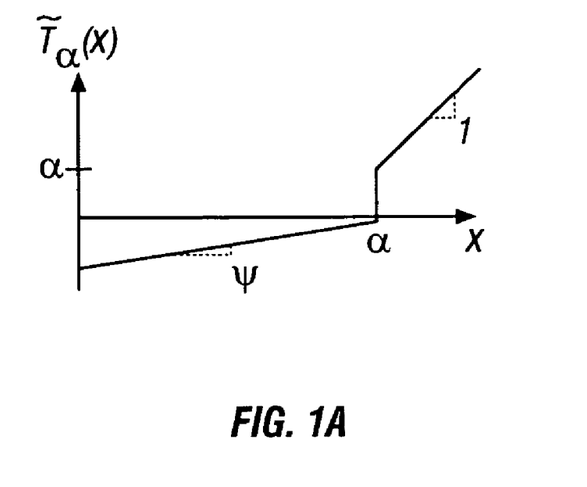
FIGS. 1(a) and (b) are graphical representations of the preferred basic functions of a first embodiment of the invention.
Figure 1B:
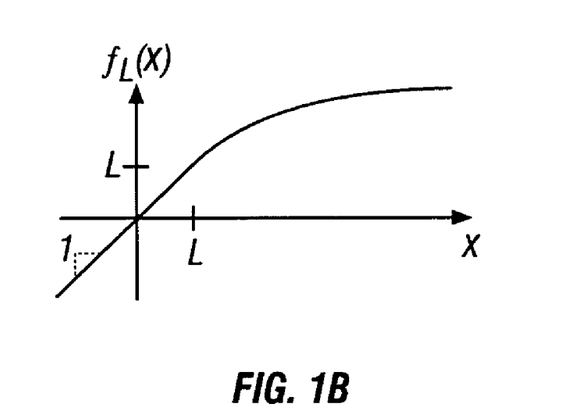

The Heaviside step function is defined as $$H_\alpha(x) = \begin{cases} 0, & x < \alpha \\ 1, & \text{otherwise} \end{cases}.$$

One approximates the threshold-linear function as $$\tilde{\tau}_\alpha(x) = x(H_\alpha(x) + \psi H_{-\alpha}(-x)), \quad (1)$$

where $\psi \in (0,1)$ is some small, positive constant to ensure that its derivative is nonzero. In the experiments, the setting was typically 0.01. For convenience, write $$\tilde{\tau}'_\alpha(x) = \frac{d}{dx}\tilde{\tau}_\alpha(x).$$

The piecewise-continuous compression function used in the SCF is defined as $$f_L(x) = \begin{cases} x, & 0 \le x \le L \\ L\log_e \frac{xe}{L}, & \text{otherwise} \end{cases}. \quad (2)$$

Note that Equation 2 has a continuous derivative that is nonzero everywhere, except as $x \to \infty$. In the experiments, one typically set L=3. For convenience, write $$f'_L(x) = \frac{d}{dx}f_L(x).$$

Equation 1 and Equation 2 are both more easily demonstrated in graphical form and are shown in FIGS. 1(a) and (b).

Define the tristate function as $$\vartheta_{\alpha,\beta}(x) = \begin{cases} 0, & x < \alpha \\ 1, & x > \beta \\ -1, & \alpha \le x \le \beta \end{cases}$$

where $\alpha < \beta$. In the experiments, one typically set $\alpha=0.4$ and $\beta=0.6$.

Let the vector of inputs at time n be $r_n \in \Re^d$, where d is the number of sensors. Let the vector of estimated activation levels of the situations at time n be $\hat{x}_n \in \Re^c$, where c is the number of situations to classify. The dynamical equations are $$u_n = \tilde{\tau}_{60}(r_n)$$

$$y_n = A\hat{x}_{n-1} - f_L(Bu_n),$$

$$\hat{x}_n = f_L(\tilde{\tau}_\beta(y_n)) \quad (3)$$

where A is the (c×c) matrix of feedback weights, and B is the (c×d) matrix of feedforward weights. From a high-level perspective, the general form of Equation 3 implies that the current driving situations are a function of previous driving situations and the current sensor inputs.

Except in trivial cases, there does not exist a closed-form optimal solution for the parameters of Equation 3, given a sequence of known sensor inputs and desired output trajectory. Therefore, any learning algorithm will rely on iterative procedures to compute locally optimal estimates of A and B. To minimize the error between the ground-truth labels and the estimated labels from Equation 3, one may pursue two different approaches. The first uses a gradient-descent approach and the second uses a Genetic Algorithm (GA) formulation.

According to the human labelers, the majority of the time (52%) during the experiments, none of the target situations occurred. The most common driving situation, "Begin Overtaken," occurs 28% of the time, while the rarest situation, "Entering On-ramp or High-Speed Roadway," occurs less than 1% of the time. Given this imbalanced data set, a typical least-squares estimation procedure, such as regression, will tend to generate only false negatives because it can achieve 99% accuracy by simply classifying "Not Entering On-ramp." By raising the "punishment" for misclassifying rare situations, a system will be forced to learn the causes of those rare, but important, events. One can do this by weighting the samples inversely proportional to how frequently they occur, one of several well-established approaches to the "rare-event problem". With such a weighting scheme, incorrectly classifying a time sample as "Entering On-ramp" (false positive) results in the error being weighted by 0.01, whereas missing a classification of "Entering On-ramp" (false negative) results in an error weight of 0.99. This has the effect of minimizing the number of false negatives, which is important in designing a system that mitigates against potentially difficult, though infrequent, driving situations. Let N be the total number of labeled samples gathered during the experiments. Let $N_i$ be the number of samples where the ith situation was "active," according to the ground-truth labels. Define the weighting function as $$\omega(x_i^*) = \begin{cases} 1 - \frac{N_i}{N}, & x_i^* = 1 \\ \frac{N_i}{N}, & x_i^* = 0 \end{cases} \quad (4)$$

In the experiments, it was found that a classifier performs much better when incorporating this weighting scheme. This is because it is impossible for a system classifying situations based solely on their relative frequency to achieve better than 50% correct when weighting classifications by Equation 4.

One preferably chooses error similar to that of large-margin classification, where learning focuses on finding the most constraining vectors to shatter a training set. Consider that an estimated situation is correct if it is "near" the target label, i.e., if the tristate value of the estimated situation equals the target label, $\vartheta_{\alpha,\beta}(\hat{x}_i)=x^*_i$. Define the error between the label for the ith situation as $$\varepsilon(x^*_i, \hat{x}_i) = \begin{cases} 0, & \vartheta_{\alpha,\beta}(\hat{x}_i) = x^*_i \\ \omega(x^*_i)(x^*_i - \hat{x}_i), & \text{otherwise} \end{cases} \quad (5)$$

The supervised-learning formulation is finding the parameter matrices A and B from Equation 3 that minimize the sum-squared error $$(\hat{A}^*, \hat{B}^*) = \underset{(A,B)}{\operatorname{argmin}} \frac{1}{2} \sum_{n=0}^{N-1} \|\varepsilon(x^*_n, \hat{x}_n)\|^2. \quad (6)$$

Both the gradient descent and the genetic algorithm seek locally optimal solutions to Equation 6.

In the gradient-descent formulation, one seeks to minimize the error measure between the target and estimated labels by tuning the parameters according to the gradient of the error. To do this, one needs the gradients of Equation 5 with respect to the parameters of Equation 3, namely the feedback matrix A and the feedforward matrix B. At time n, let the estimated situation activation for the ith situation be $[\hat{x}_n]_i$ from Equation 3 and let the corresponding ground-truth label be $[\hat{x}^*_n]_i$. The gradient of the error measure with respect to the feedforward weights at time n for the ith situation label is then $$\frac{\partial}{\partial [A]_{i,j}} \frac{1}{2} \|\varepsilon([x^*_n]_i, [\hat{x}_n]_i)\|^2 = \begin{cases} 0, & \vartheta_{\alpha,\beta}([\hat{x}_n]_i) = [x^*_n]_i \\ -\omega([x^*_n]_i)([x^*_n]_i - [\hat{x}_n]_i) \frac{\partial}{\partial [A]_{i,j}} [\hat{x}_n]_i, \end{cases}$$

otherwise

One must now apply the chain rule several times and, skipping some lengthy steps, one receives the following result:

$$\frac{\partial [\hat{x}_n]_i}{\partial [A]_{i,j}} = f'_L(\tilde{\tau}_\beta([y_n]_i))\tau'_\beta([y_n]_i)\left([\hat{x}_{n-1}]_j + \left[A \frac{\partial \hat{x}_{n-1}}{\partial [A]_{i,j}}\right]_i\right). \quad (7)$$

To compute the full gradient, it is necessary to vary the indices (i and j) over all possibilities. The derivation of the feedforward weights is similar to Equation 7, the result being:

$$\frac{\partial [\hat{x}_n]_i}{\partial [B]_{i,j}} = f'_L(\tilde{\tau}_\beta([y_n]_i))\tau'_\beta([y_n]_i)\left(\left[A \frac{\partial \hat{x}_{n-1}}{\partial [B]_{i,j}}\right]_i + f'_L([Bu_n]_i)[u_n]_j\right). \quad (8)$$

Note that both Equation 7 and Equation 8 use the gradient from the previous time step, which could lead to unstable updates as the error accumulates. Various researchers in the field of adaptive control have identified sufficient conditions to ensure that gradient-descent update rules yield stable estimates. The pseudo-code for the preferred gradient-descent algorithm is shown below, where $\{x^*_0, \ldots, x^*_N\}$ is the sequence of target labels, $\{r^*_0, \ldots, r^*_N\}$ is the sequence of sensor inputs, $\eta \in (0,1)$ is the step size, and $\sigma>0$ is the stopping criterion.

```
v:=∞
while v>σ
    v:=0
    for all r_n ∈ {r_0, ..., r_N}
        Compute x̂_n as Equation 3
```

$$\Delta_A := \frac{\partial}{\partial A} \frac{1}{2} \|\varepsilon([x^*_n]_i, [\hat{x}_n])\|^2$$

as Equation 7

$$\Delta_B := \frac{\partial}{\partial B} \frac{1}{2} \|\varepsilon([x^*_n]_i, [\hat{x}_n])\|^2$$

as Equation 8
```
    A:=A−η Δ_A
    B:=B−η Δ_B
    v:=v+‖Δ_A‖_F+‖Δ_B‖_F
    end for all
end while
```

It can be shown that the algorithm and update rules are stable, and consequently guaranteed to converge and terminate at a local minimum, if the step size η is decayed in the standard manner.

For the genetic algorithm embodiment, the DAKOTA optimization package was employed to create a Genetic Algorithm (GA) to find locally optimal solutions for the parameters of the dynamical system in Equation 3. The genome is preferably simply a column-stacked vector of the feedforward and feedback matrices, y=vec([A;B]). The fitness criterion for a given parameterization was the error measure between all ground-truth and estimated labels, as in Equation 6, which is the same as the gradient-descent formulation. Between generations, keep the N best genomes and the stochasticity is preferably handled solely by genome mutations, as crossover was not allowed for. The genome mutations were selected by sampling from a Gaussian distribution centered about the keeper genome from the previous generation, $y^{(i+1)} \sim N(y^{(i)}, \Sigma)$. The covariance matrix, $\Sigma$, was determined by hand a priori to contain reasonable values.

Figure 2:
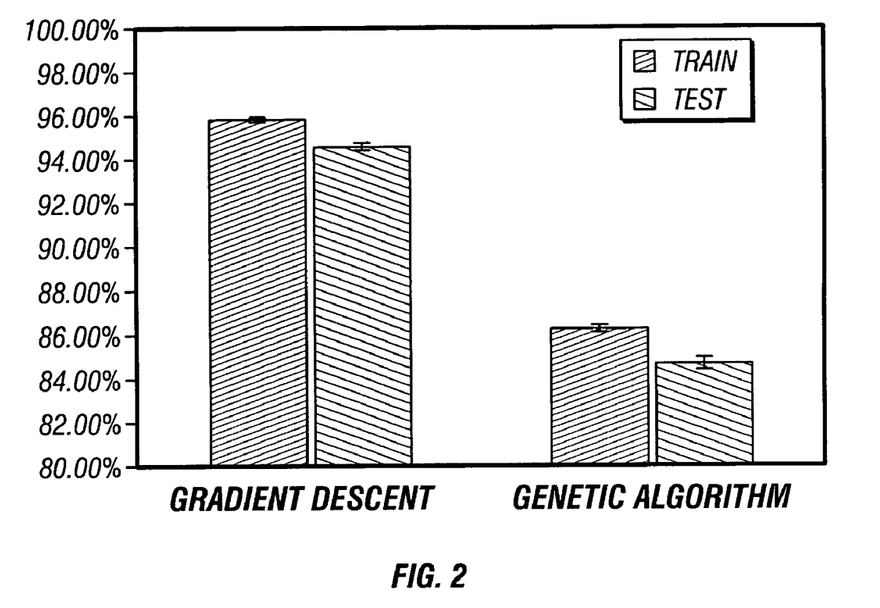
FIG. 2 is a graph of the results of a gradient descent and genetic algorithm for estimating the correct situation; the error bars indicate the 99% confidence interval.
Figure 3:
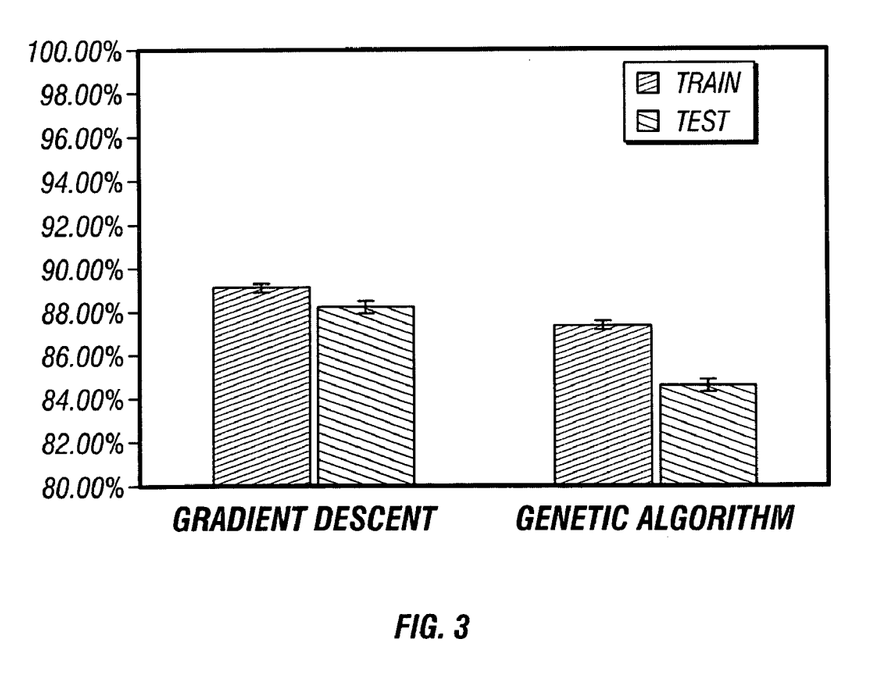
FIG. 3 is a graph of the results of the gradient descent and genetic algorithm for estimating the weighted correct situation; the error bars indicate the 99% confidence interval.

The driving data was divided into a training set (18.3 hours) and a test set (5.6 hours). Each of the five subjects drove the roadway circuit three times. Each driver had two circuits randomly assigned to the training set and one to the test set. Both the gradient-descent and genetic-algorithm formulations were run on these data sets. In every performance statistic that was measured, the gradient-descent algorithm outperformed the genetic algorithm. FIG. 2 shows the performance in absolute percentage correct. The gradient-descent algorithm predicted the human recognition of driving situations over 95% of the time on the test set, while the GA managed about 85% correct. As mentioned earlier, a most important statistic in measuring the success of the algorithms is the weighted percentage correct (Equation 4). FIG. 3 shows the performance in weighted percentage correct. When weighting the classification score by Equation 4, the gradient-descent algorithm predicted human recognition of driving situations about 88% of the time on the test set, while the GA managed about 84% correct. The gradient-descent algorithm is also much more efficient at finding a solution than the GA. On the 18.3 hours driving data in the training set, the gradient descent algorithm typically converged in about one hour of computation time and 101 parameter evaluations. The GA, on the other hand, averaged 1611 hours (about 67 days) of computation time and 50,013 evaluations. The relative efficiency of the gradient-descent algorithm is due to the massive amount of problem-specific knowledge incorporated into the algorithm—the gradient of the error. Since this information is not incorporated into the GA, it is not surprising that it used substantially more parameter evaluations to arrive at a locally optimal solution. However, even when the GA was given the solution of the gradient-descent algorithm as its initial genome, the GA was unable to improve performance after several machine-days of computation.

The identification and extraction of patterns from observed data goes back to ancient times, and pattern recognition is now a necessary capability in many fields. Researchers are still developing novel methods to identify and extract patterns from large amounts of data. Other researchers are interested in identifying contexts, or situations, in response to human behavior to improve system performance, with applications in computing and mobile phones.

Incorporating pattern recognition to assist humans in vehicle driving has a relatively long history in robotics, most notably the Navlab project at Carnegie-Mellon University. In order to simplify the process of writing control software, the Navlab project quickly started using supervised-learning algorithms based on observations gained while humans drove the target vehicle.

In the present invention, learning algorithms were employed to estimate the optimal parameters of a nonlinear dynamical system. Broadly speaking, estimating the parameters of a dynamical system that minimize some cost function is known as optimal control. There has been a substantial amount of work in nonlinear systems, though finding optimal solutions to most nonlinear systems is generally intractable. While one is able to write down the gradient of the system with respect to the tunable parameters and derive stable update equations, this is usually quite cumbersome and time consuming. This is the reason that general stochastic optimization techniques, such as genetic algorithms, are often used to solve for the unknown optimal parameters. While the experiments herein compared the performance of a designed gradient-descent algorithm to a standard genetic-algorithm formulation, there are a large number of other techniques to classify time-series data that could be employed with the present invention, including recurrent neural networks and hidden Markov models.

The second embodiment of the invention is next described.

Figure 5:
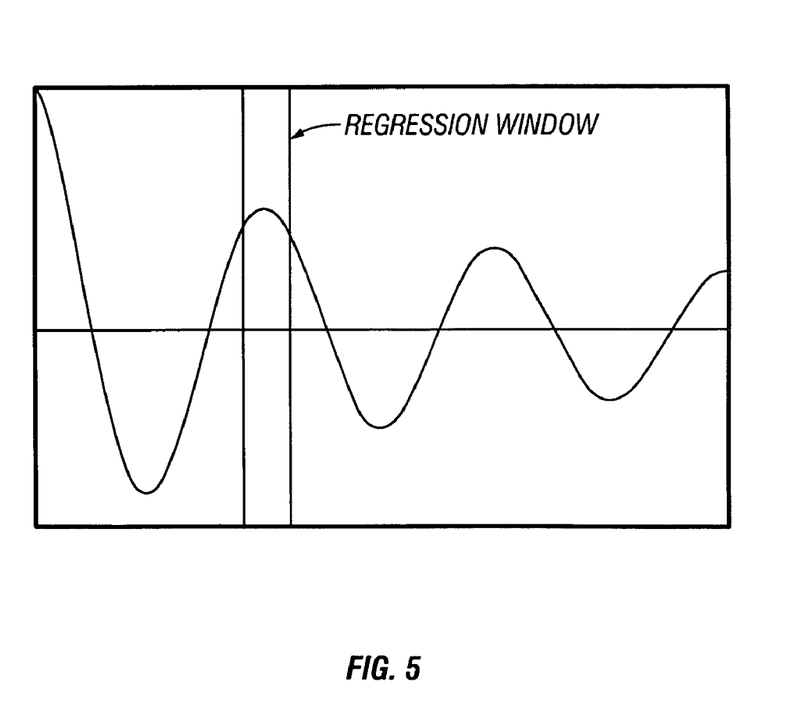
FIG. 5 illustrates taking a temporal signal, focusing on the regression window.
Figure 6:
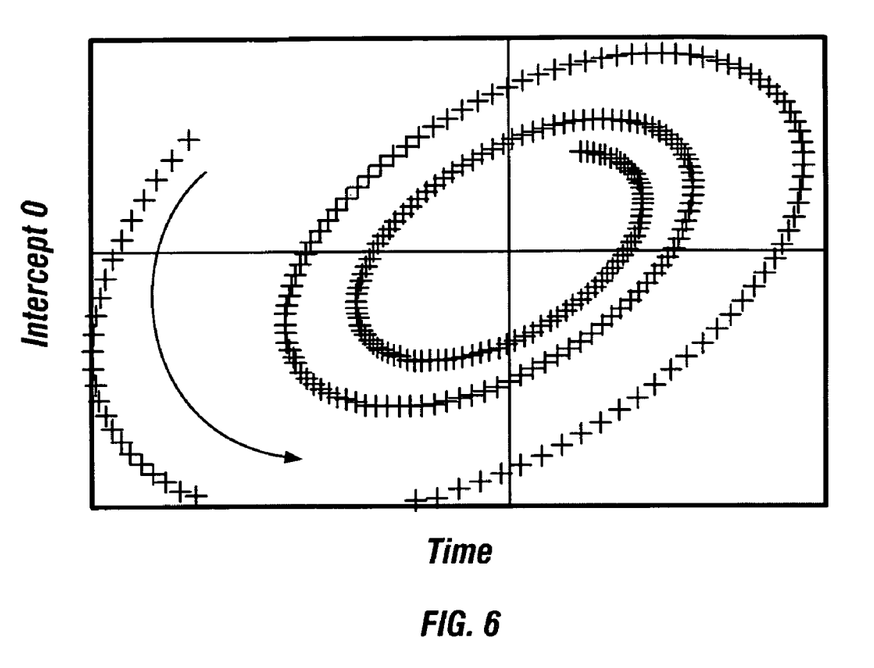
FIG. 6 shows the regression coefficients from FIG. 5; the cross marks the coefficients from the regression window in FIG. 5.
Figure 7:
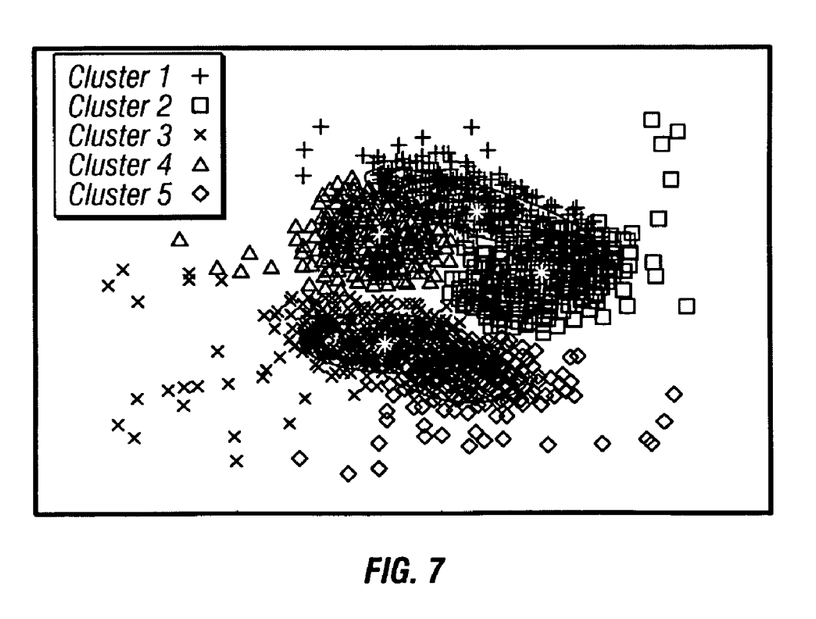
FIG. 7 is a two-dimensional representation of a clustering example.

The manner by which the contexts are generated in the second embodiment of the invention uses an approach called "unsupervised learning." The form of unsupervised learning that is preferred attempts to find regularities in the data. This is done by first transforming temporal sensory signals into a high-dimensional vector. It is preferred to use linear regression to fit a straight line to a temporal signal over a predefined time window, shown in FIG. 5, resulting in regression coefficients shown in FIG. 6. The slope (m) and offset (b) values are two coordinates in a vector space. For N sensors, this regression approach yields a 2*N dimensional vector. The preferred unsupervised learning algorithm searches for "clusters" in this high-dimensional vector space, as shown in FIG. 7. One of the assumptions of this work is that regularities in this vector space are caused by underlying physical contexts. For example, entering an onramp will result in the driver accelerating, putting on a turn signal, and looking over her shoulder. It is this type of regularity that the second embodiment's algorithm captures.

Once the classifier is constructed, and new sensory data are being input into the system, one estimates the vector-space parameters from the regression mentioned above, using a buffer to keep the data on hand. The classifier estimates the probability that the vector-space parameters were generated by each of the k clusters. This probability distribution is the output of the classifier.

Figure 4:
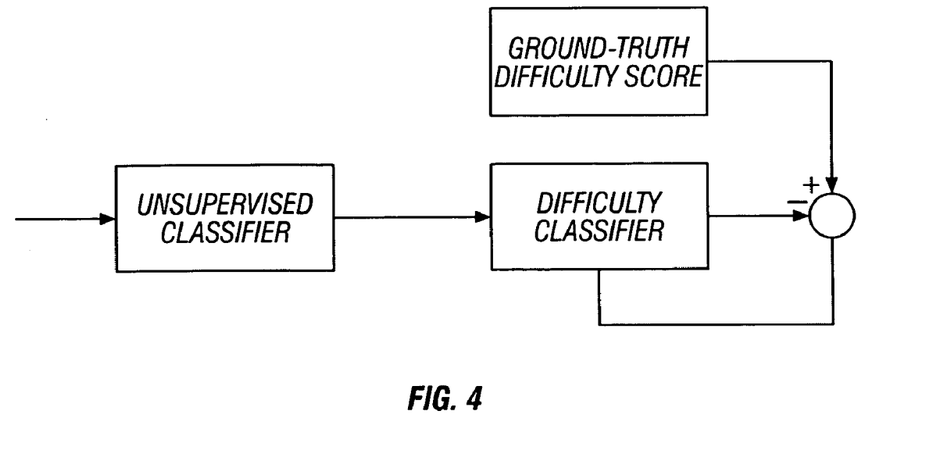
FIG. 4 is a diagram of training the difficulty classifier of a second embodiment of the invention.

To perform difficulty classification, as shown in FIG. 4, one obtains a time series of difficulty estimates from a human, and these human-scored difficulty estimates are analog (e.g., 0-100) and are diagnostic of the context classifier. To estimate the "optimal" difficulty classifier, one takes the time series of context probabilities from the unsupervised context classifier as input and the human-scored difficulty estimates as ground truth. One then estimates a cognitive model (using the approach described in the first embodiment) that optimally predicts the human perception of difficulty, also on an analog scale of, e.g., 0-100, using the context probabilities as input.

To adapt a system to a new user, suppose one has a context classifier constructed from the approach mentioned above that is constructed from the data of a group of people for which we have human-scored difficulty estimates. Then a new user, for whom we do not have difficulty estimates, begins driving the vehicle. In the second embodiment one can adapt the previously constructed context classifier to the unique driving style of this new user. As data from the new user becomes available, simply add these to the training set mentioned above and run the unsupervised-learning algorithms to update the locations of the contexts, resulting in an adapted context classifier. One then uses the probability distributions from the adapted classifier to estimate a new optimal difficulty classifier using only the inputs and outputs for which one has human-scored difficulty estimates. While such an approach may initially sound costly, it can be computed in real time in parallel with the regular operation of the context classification.

The present invention, in either embodiment, may be conjoined with a motor vehicle and concomitant sensor inputs in a variety of hardware implementations. For example, the data processing can be performed by an appropriately programmed microprocessor, Application Specific Integrated Circuit (ASIC), Field Programmable Gate Array (FPGA), or the like, in conjunction with appropriate memory and bus elements. The methods of the invention can be implemented by appropriate software coded in C++, Java, microcode, etc., as understood by one of ordinary skill in the art.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of enhancing safety for an operator of a motor vehicle, the method comprising the steps of:
    employing a plurality of sensors of vehicle and operator conditions;
    matching collective output from the sensors against a plurality of known dangerous conditions; and
    preventing certain activity of the operator if a known dangerous condition is detected; and
    wherein the matching step comprises matching against a plurality of conditions known a priori but as determined from a plurality of test subjects experiencing simulations of those conditions and from the sensor data received during recording of those simulations.

2. The method of claim 1 wherein the matching step comprises employing a nonlinear dynamical system.

3. The method of claim 2 wherein in the matching step an optimal solution of a learning algorithm of the nonlinear dynamical system has been calculated.

4. The method of claim 3 wherein in the matching step false negatives are substantially reduced in the calculation of an optimal solution via a method selected from the group consisting of gradient-descent methods and genetic algorithm methods.

5. The method of claim 2 wherein the matching step comprises matching against a plurality of known conditions as determined automatically from collected sensor data of those conditions and from concomitant human-scored difficulty estimates.

6. The method of claim 5 wherein the matching step comprises matching against a plurality of known conditions as determined via unsupervised learning from collected sensor data of those conditions and from concomitant human-scored difficulty estimates.

7. The method of claim 6 wherein the matching step comprises matching against a plurality of known conditions as determined via unsupervised learning employing linear regression of a 2*N dimensional vector of sensor input from N sensors.

8. The method of claim 5 additionally comprising allowing the operator to make difficulty estimates concerning current conditions, which estimates are then incorporated into the matching step.

9. The method of claim 1 wherein the preventing step comprises preventing one or more activities from the list consisting of employing a telephone, listening to audio programs, listening to high-volume audio programs, and employing vehicle interior lighting.

10. A physical storage device having machine executable code stored therein, which when executed by a computer enhances the safety for an operator of a motor vehicle, the device comprising code for:
receiving data from a plurality of sensors of vehicle and operator conditions;
matching collective output from the sensors against a plurality of known dangerous conditions; and
preventing certain activity of the operator if a known dangerous condition is detected; and
wherein the matching code comprises code matching against a plurality of conditions known a priori but as determined from a plurality of test subjects experiencing simulations of those conditions and from the sensor data received during recording of those simulations.

11. The storage device of claim 10 wherein the matching code comprises code implementing a nonlinear dynamical system.

12. The storage device of claim 11 wherein the matching code derives from an optimal solution of a learning algorithm of the nonlinear dynamical system.

13. The storage device of claim 12 wherein the matching code comprises code in which false negatives are substantially reduced via the calculation of an optimal solution via a method selected from the group consisting of gradient-descent methods and genetic algorithm methods.

14. The storage device of claim 11 wherein the matching code comprises code matching against a plurality of known conditions as determined automatically from collected sensor data of those conditions and from concomitant human-scored difficulty estimates.

15. The storage device of claim 14 wherein the matching code comprises code matching against a plurality of known conditions as determined via unsupervised learning from collected sensor data of those conditions and from concomitant human-scored difficulty estimates.

16. The storage device of claim 15 wherein the matching code comprises code matching against a plurality of known conditions as determined via unsupervised learning employing linear regression of a 2*N dimensional vector of sensor input from N sensors.

17. The storage device of claim 14 additionally comprising code allowing the operator to make difficulty estimates concerning current conditions, which estimates are then incorporated into operations of the matching code.

18. The storage device of claim 10 wherein the preventing code comprises code preventing one or more activities from the list consisting of employing a telephone, listening to audio programs, listening to high-volume audio programs, and employing vehicle interior lighting.

19. A method of enhancing safety for an operator of a motor vehicle, the method comprising the steps of:
employing a plurality of sensors of vehicle and operator conditions;
matching collective output from the sensors against a plurality of known dangerous conditions; and
preventing certain activity of the operator if a known dangerous condition is detected; and
wherein the matching step comprises matching against a plurality of known conditions as determined automatically from collected sensor data of those conditions and from concomitant human-scored difficulty estimates.

20. The method of claim 19 wherein the matching step comprises matching against a plurality of known conditions as determined via unsupervised learning from collected sensor data of those conditions and from concomitant human-scored difficulty estimates.

21. The method of claim 20 wherein the matching step comprises matching against a plurality of known conditions as determined via unsupervised learning employing linear regression of a 2*N dimensional vector of sensor input from N sensors.

22. The method of claim 19 additionally comprising allowing the operator to make difficulty estimates concerning current conditions, which estimates are then incorporated into the matching step.

23. A physical storage device having machine executable code stored therein, which when executed by a computer enhances the safety for an operator of a motor vehicle, the device comprising code for:
receiving data from a plurality of sensors of vehicle and operator conditions;
matching collective output from the sensors against a plurality of known dangerous conditions; and
preventing certain activity of the operator if a known dangerous condition is detected; and
wherein the matching code comprises code matching against a plurality of known conditions as determined automatically from collected sensor data of those conditions and from concomitant human-scored difficulty estimates.

24. The storage device of claim 23 wherein the matching code comprises code matching against a plurality of known conditions as determined via unsupervised learning from collected sensor data of those conditions and from concomitant human-scored difficulty estimates.

25. The storage device of claim 24 wherein the matching code comprises code matching against a plurality of known conditions as determined via unsupervised learning employing linear regression of a 2*N dimensional vector of sensor input from N sensors.

26. The storage device of claim 23 additionally comprising code allowing the operator to make difficulty estimates concerning current conditions, which estimates are then incorporated into operations of the matching code.

* * * * *